US00PP29800P2

(12) United States Plant Patent
Hanslik

(10) Patent No.: US PP29,800 P2
(45) Date of Patent: Nov. 6, 2018

(54) ***ILEX* PLANT NAMED 'MADEZ'**

(50) Latin Name: ***Ilex* x *meserveae***
Varietal Denomination: Madez

(71) Applicant: Paul Charles Hanslik, Geneva, OH (US)

(72) Inventor: Paul Charles Hanslik, Geneva, OH (US)

( * ) Notice: Subject to any disclaimer, the term of this patent is extended or adjusted under 35 U.S.C. 154(b) by 0 days.

(21) Appl. No.: 15/731,806

(22) Filed: Aug. 3, 2017

(51) Int. Cl.
*A01H 5/12* (2018.01)

(52) U.S. Cl.
USPC ..... Plt./247
CPC ..... *A01H 5/12* (2013.01)

(58) Field of Classification Search
USPC ..... Plt./247
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Ilex* cultivar named 'Madez' which is characterized by an upright and freely branching growth habit, a conical plant shape, excellent cold hardiness, strong plant vigor, very glossy juvenile foliage with a general coloration appearing as a combination of deep maroon and dark brown, dark green and very glossy mature foliage, and vibrant red berries through the winter. The claimed plant propagates successfully by softwood stem cuttings and has proven to be uniform and stable in the resulting generations.

3 Drawing Sheets

Latin name of the genus and species: The Latin name of the genus and species of the novel variety disclosed herein is *Ilex* x *meserveae*.

Variety denomination: The inventive variety of *Ilex* x *meserveae* disclosed herein has been given the variety denomination 'Madez'.

BACKGROUND OF THE INVENTION

Parentage: The claimed plant is an openly pollinated seedling selection which was found at a commercial ornamental plant nursery in Madison, Ohio. In 2009, a seedling with deep maroon foliage and an upright, conical growth habit was discovered amongst a plurality of *Ilex* hybrid cultivars growing in close proximity to one another in a display garden. Cultivars growing in the garden, and therefore the potential parent plants, include 'Blue Princess', 'Blue Prince', 'Blue Girl', 'Blue Boy', 'Mesog' (U.S. Plant Pat. No. 4,878), 'Mesdob' (U.S. Plant Pat. No. 4,803), 'Mesid' (U.S. Plant Pat. No. 4,685), and 'Meschick' (U.S. Plant Pat. No. 4,996). The true parentage of the claimed plant is not known but the presumed female parent is 'Meschick' due to similarities in growth habit and foliage characteristics. The seedling was isolated and grown to a mature size to confirm the distinctness and stability of the characteristics initially observed. After further evaluation and confirmation of the desirable traits, the claimed plant was finally selected for commercialization in 2016 and given the breeder denomination, 'Madez'.

Asexual Reproduction: In 2009, 'Madez' was first asexually reproduced in Geneva, Ohio by way of softwood stem cuttings. The claimed plant was found to asexually reproduce in uniform and stable manner and 6 successive cycles of vegetative propagation have proven to be true to type.

SUMMARY OF THE INVENTION

The following characteristics have been repeatedly observed and represent the distinguishing characteristics of the new *Ilex* cultivar 'Madez'. These traits, in combination, distinguish 'Madez' as a new and distinct cultivar.

1. 'Madez' exhibits an upright, freely branching growth habit and a conical plant shape; and
2. 'Madez' exhibits excellent cold hardiness and strong plant vigor; and
3. 'Madez' exhibits very glossy juvenile foliage with a general coloration appearing as a combination of deep maroon and dark brown; and
4. 'Madez' exhibits juvenile foliage which becomes increasingly suffused with dark green as it matures; and
5. 'Madez' exhibits dark green and very glossy mature foliage which has an elongated ovate shape with spinose margins and a cuspidate apex; and
6. 'Madez' exhibits medium-sized, vibrant red berries.

BOTANICAL DESCRIPTION OF THE PLANT

Figure 1:
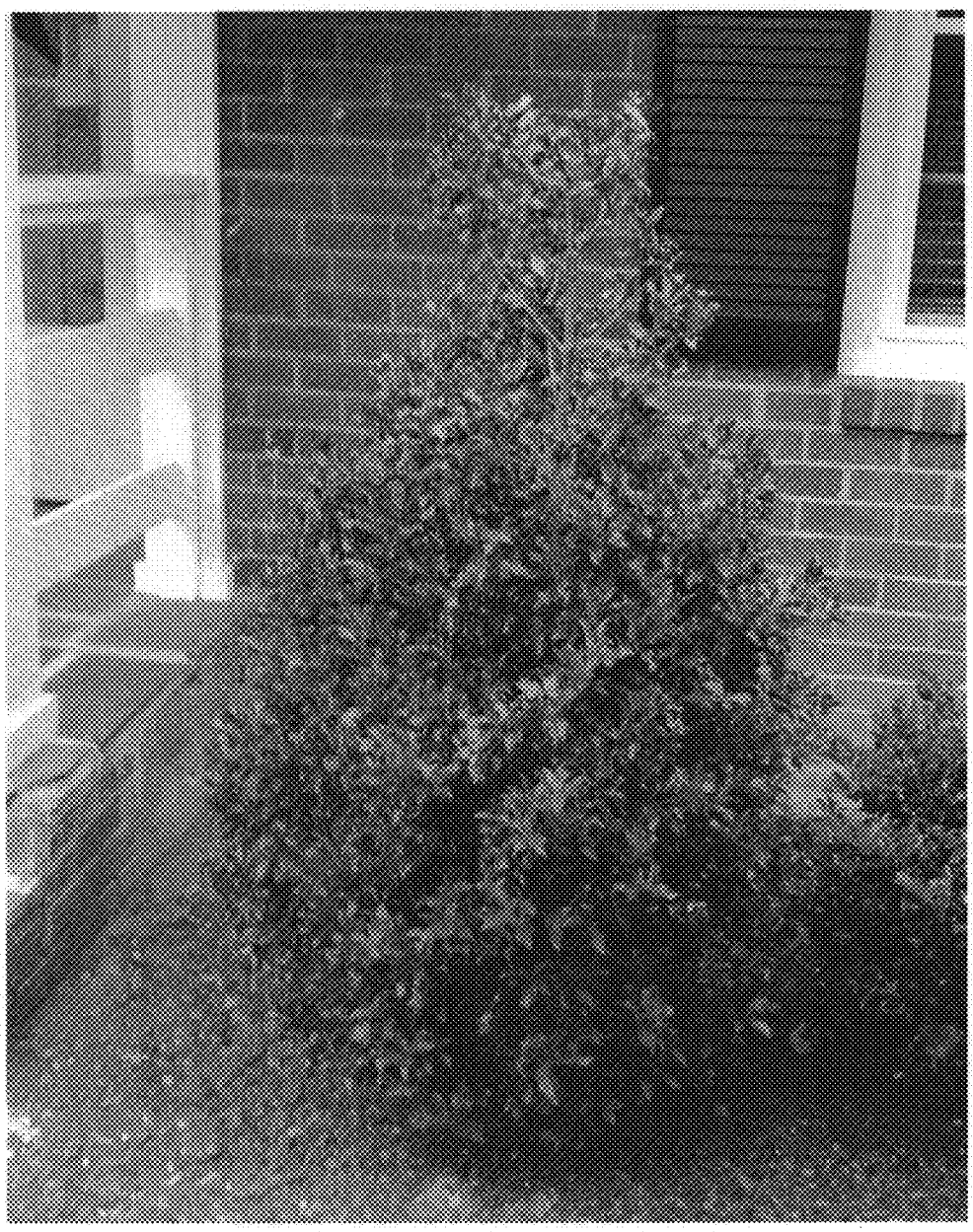
FIG. 1 illustrates, as nearly true as it is reasonably possible to make the same in color photographs of this type, an exemplary 4 year old field-grown 'Madez' plant in Geneva, Ohio.
Figure 2:
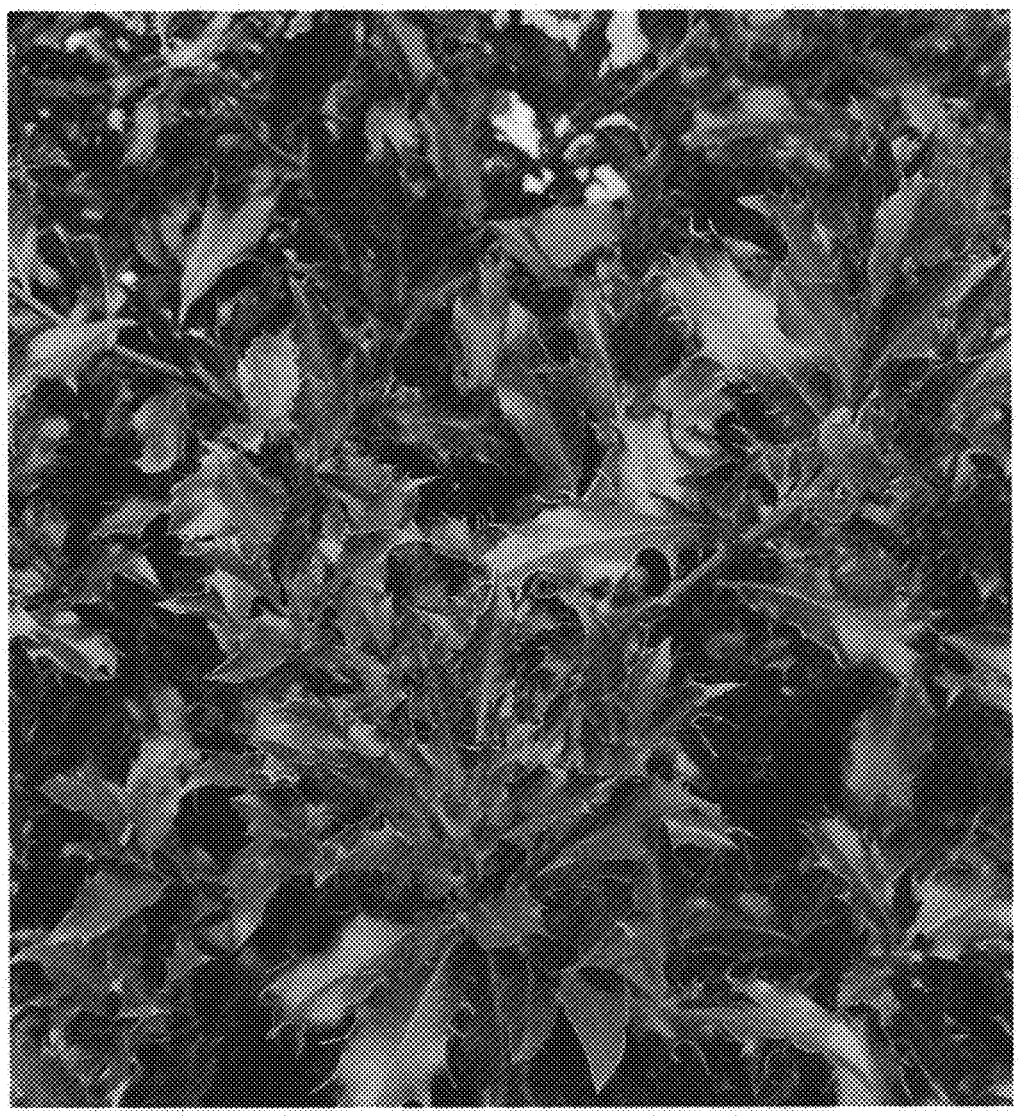
FIG. 2 illustrates, as nearly true as it is reasonably possible to make the same in color photographs of this type, the typical juvenile, intermediate and mature foliage of 'Madez'.
Figure 3:
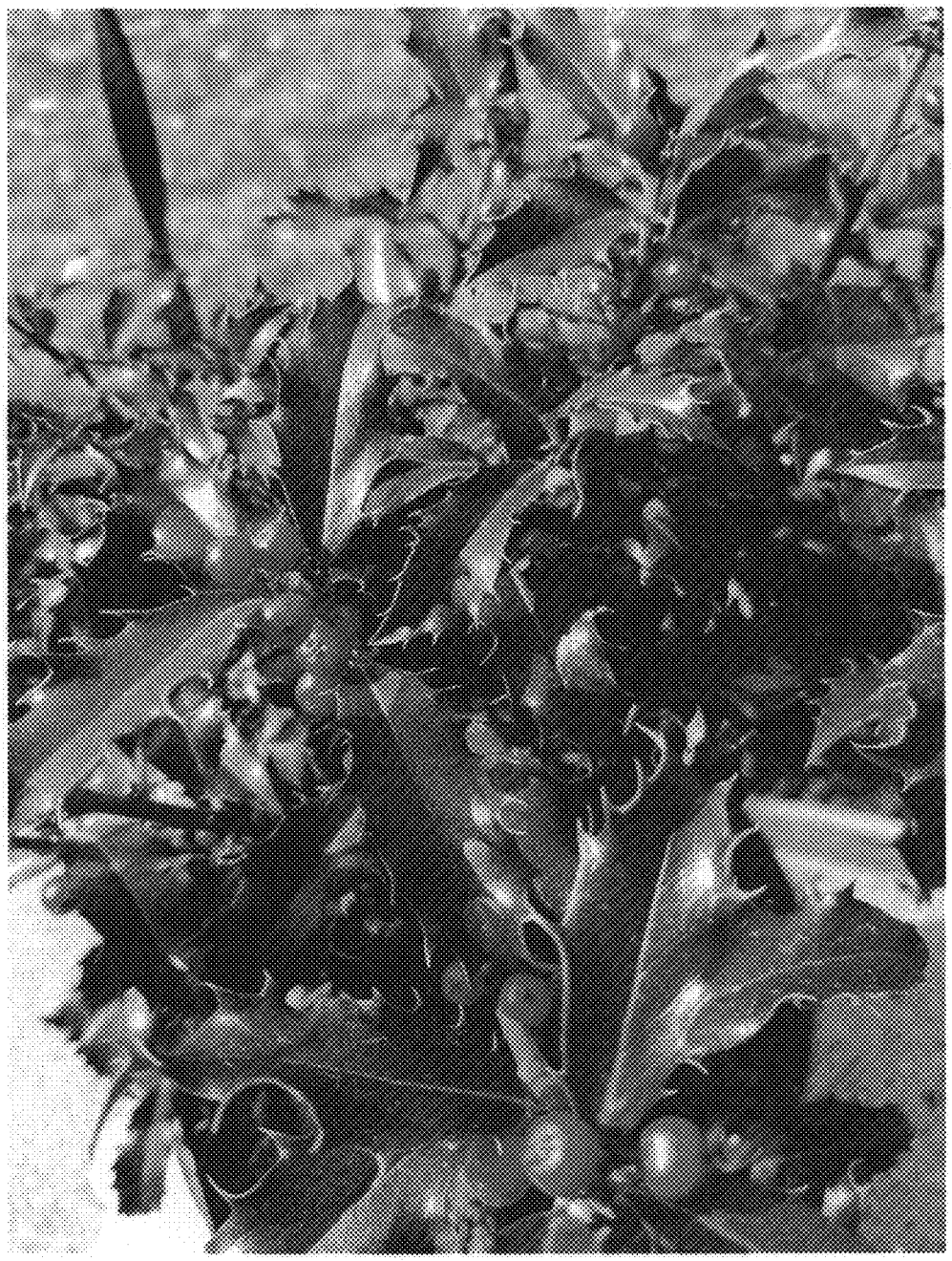
FIG. 3 illustrates, as nearly true as it is reasonably possible to make the same in color photographs of this type, the typical berries of 'Madez'.

The following is a detailed botanical description of a new and distinct *Ilex* cultivar known as 'Madez'. Plant observations were made using 3 gallon greenhouse-grown plants produced in Geneva, Ohio. Unless indicated otherwise, the descriptions disclosed herein are based upon observations made of a 3 year old 'Madez' plant grown using conventional production techniques for this species. The observed plant was grown in full exposure to natural sunlight, maintained with granular slow release fertilizer, and regularly watered with overhead irrigation. Preventative fungicide was applied at the time of propagation, but no pest or disease measures were employed thereafter during production. Observation data was recorded in April of 2017.

Those skilled in the art will appreciate that certain characteristics will vary with older or, conversely, younger plants. 'Madez' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition except where common terms of color are used.

A botanical description of 'Madez' and comparisons with the presumed parent and most similar commercial cultivar are provided below.

General plant description:

*Plant habit*.—Dioecious broadleaf evergreen with an upright, freely branching growth habit. 'Madez' is a female plant.

*Plant shape*.—Conical; approximately 2.5 to 3 times taller than wide.

*Height*.—Approximately 150 cm at 5 years of age.

*Width*.—Approximately 75 cm at 5 years of age.

*Environmental tolerances*.—Hardy in U.S. Hardiness Zone 5b; can be produced in sandy to loamy soils; dry to moderately moist soils; full sun to moderate shade.

*Pest and disease susceptibility or resistance*.—Plants have not been observed to be susceptible or resistant to pathogens and pests common to *Ilex* x *meserveae*.

*Propagation*.—Propagation is accomplished using softwood stem cuttings from July through December in Zone 5.

*Time to develop roots*.—Approximately 6 to 8 weeks, under mist irrigation with bottom heat at 65 degrees Fahrenheit.

*Crop time*.—Approximately 4 to 5 months, from spring through summer in Geneva, Ohio, are needed to produce a 6 to 8 inch tall fully rooted cutting; two growing seasons will produce a well-formed 15 to 18 inch tall finished plant.

Root system:

*Description*.—A network of non-fibrous, non-fleshy roots.

*Rooting habit*.—Freely branching, moderately dense, and evenly distributed throughout the soil profile.

*Color, juvenile roots*.—Yellow-white, RHS 158B.

*Color, mature roots*.—Greyed-orange, RHS 166C.

Stems:

*Branching habit*.—A near-vertical central main stem, occasionally branched, gives rise to numerous lateral branches. Main stems — Quantity — One; occasionally branching. Attitude — Erect; near vertical. Cross section — Generally circular. Diameter — 25 mm, at the base of the trunk. Color — A combination of yellow-green (RHS 146A), greyed-green (RHS 197A), and greyed-brown (RHS 199D). Texture — Smooth, glabrous; lenticels present. Lenticels are elliptical; approximately 1.0 mm long and 0.75 mm wide; color is greyed-brown, RHS 199D. Strength — Very strong. Lateral branches — Stem angle to main axis — In between 45 and 60 degrees. Cross-section — Circular; somewhat angular. Diameter — 4.5 mm at the base. Internode length — Varying from 5 to 8 mm. Color, juvenile — Yellow-green, RHS 146B. Color, mature — A combination of yellow-green (RHS 146A), greyed-green (RHS 197A), and greyed-brown (RHS 199D). Texture — Smooth, glabrous; lenticels present at and near the base. Lenticels are elliptical; approximately 1.0 mm long and 0.75 mm wide; color is greyed-brown, RHS 199D. Stem strength — Strong.

Foliage:

*Arrangement*.—Alternate.

*Attachment*.—Petiolate.

*Division*.—Simple.

*Shape*.—Ovate.

*Length*.—65 mm.

*Width*.—33 mm, including the marginal spines.

*Apex*.—Acuminate.

*Base*.—Cuneate.

*Margin*.—Spinose.

*Aspect*.—Heavily reflexed.

*Texture and pubescence, adaxial surface*.—Smooth, glabrous, and very glossy.

*Texture and pubescence, abaxial surface*.—Smooth, glabrous and matte.

*Color*—Juvenile foliage, adaxial surface — General deep maroon coloration, nearest to in between greyed-purple RHS 183A, red-purple RHS 59A and brown RHS 200A; suffused with yellow-green, RHS 147A. Juvenile foliage, abaxial surface — Generally a deep maroon coloration, nearest to in between red-purple RHS 59A and brown RHS 200A. Mature foliage, adaxial surface — Yellow-green, nearest to RHS 147A but darker. Mature foliage, abaxial surface — Yellow-green, RHS 148B.

*Venation*.—Pattern — Pinnate. Vein color, adaxial surface — The midrib and all secondary veins are yellow-green, nearest to RHS 144A. Vein color, abaxial surface — The midrib and all secondary veins are yellow-green, nearest to RHS 144B.

*Petiole*.—Length — 8.0 mm. Diameter — 2.0 mm. Color, adaxial surface — Yellow-green, RHS 144A. Color, abaxial surface — Yellow-green, RHS 144B. Texture, adaxial and abaxial surfaces — Smooth; glabrous.

Inflorescence:

*Type*.—Solitary female flowers occurring at the leaf axils, with 2 to 3 flowers at each axil.

Flower bud:

*Shape*.—Round to short ovoid.

*Dimensions*.—Approximately 9 mm long and 5 mm in diameter.

*Color, upper and lower surfaces*.—Nearest to yellow-green, RHS 145D.

Flower:

*General description*.—Single rotate flowers with a shallow cup shape; flowers are female.

*Natural flowering season*.—Approximately May through early June in Madison, Ohio.

*Quantity.*—2 to 3 flowers per axil.

*Lastingness.*—Petals drop away in approximately 5 days.

*Persistence.*—Not persistent.

*Fragrance.*—Not fragrant.

*Attitude.*—Flowers held upright and slightly outward.

*Dimensions.*—Corolla is approximately 11 mm in diameter and 6 mm deep.

*Peduncle.*—Dimensions — 7 mm long and 1.5 mm in diameter. Color — Yellow-green, nearest to RHS 144C. Texture — Smooth; glabrous. Strength — Medium.

*Calyx.*—Shape — Sepals fused at the base forming a cup, with 4 rotate sepal lobes. Diameter — Approximately 4 mm. Depth — Approximately 3 mm. Quantity of sepal lobes — 4 sepal lobes. Apex, sepal lobes — Sepal lobes acute. Base — Fused. Margin — Entire. Texture, inner and outer surfaces — Smooth and glabrous. Color when opening, inner surface — Yellow-green, RHS 147C. Color when opening, outer surface — Yellow-green, RHS 147C. Color when fully open, inner surface — Yellow-green, RHS 148D. Color when fully open, outer surface — Yellow-green, RHS 148D.

*Petals.*—Quantity of petals — 4 free petals. Arrangement — Single rotate whorl. Dimensions — Approximately 8 mm long and 5 mm wide. Apex — Obtuse. Margin — Entire; slightly undulated. Aspect — Incurved. Texture, inner and outer surfaces — Smooth; glabrous. Luster, inner and outer surfaces — Matte to very slightly glossy. Color when opening, inner surface — White, RHS 155C. Color when opening, outer surface — White, RHS 155C. Color when fully open, inner surface — Nearest to green-white, RHS 157D; petals are slightly translucent. Color when fully open, outer surface — Nearest to green-white, RHS 157D; petals are slightly translucent. Petal color fading to — Not fading.

Reproductive organs:

*Androecium.*—Stamens — Quantity — 4 sterile stamens. Position — Inserted; free. Attachment — One stamen attached at the base of each petal. Overall length — Approximately 4 mm long. Filament — Dimensions — 3.5 mm long and approximately 0.5 mm in diameter. Color — Green-white, nearest to RHS 157D. Anthers — Attachment — Basifixed. Shape — Nearly globose. Dimensions — Approximately 1.0 mm long and 0.75 mm wide. Color — Green-white, nearest to RHS 157D. Pollen — None.

*Gynoecium.*—Pistils — Quantity — One; inferior to the corolla. Overall dimensions — Approximately 3.5 mm tall and 4 mm in diameter at the stigma. Stigma — Shape — Globular. Dimensions — Approximately 1 mm tall and 3 mm wide. Color — Yellow-green, RHS 152C. Style — Shape — Relatively broad, and truncated. Dimensions — Approximately 2.5 mm tall and 4 mm in diameter. Color — Yellow-green, RHS 144C. Ovary — Position — Superior. Color — Yellow-green, nearest to RHS 144C.

Fruit and seed:

*Fruit.*—Type — Simple, indehiscent berry. Shape — Globose. Quantity — 1 to 2 berries per axil, with approximately 8 to 10 berries on lateral branches. Dimensions — Approximately 8 mm in diameter, and 8 mm tall. Texture, pubescence and luster — Smooth, glabrous and glossy. Color, mature fruit — Red, nearest to RHS 45A.

*Seed.*—Quantity — Usually 4 per berry. Shape — Oblong, three-sided, with an ovate to deltoid outline. Dimensions — 4 mm long and 1.75 mm in diameter. Color — In between yellow-white, RHS 158A, and greyed-yellow, nearest to RHS 161D. Texture — Slightly rough.

COMPARISON WITH THE PRESUMED PARENT PLANT

Plants of the new cultivar 'Madez' differ from the presumed seed parent, *Ilex* hybrid 'Meschick' (U.S. Plant Pat. No. 4,996), by the characteristics described in Chart 1. The pollen parent is unknown and therefore no comparison is available.

CHART 1

| Characteristic | 'Madez' | 'Meschick' |
|---|---|---|
| General coloration of the juvenile foliage. | A combination of deep maroon and dark brown. | Green suffused with greyed-orange. |
| Length of foliage | 65 mm long. | 20 to 30 mm long. |

COMPARISON WITH THE MOST SIMILAR *ILEX* CULTIVAR KNOWN TO THE INVENTOR

Plants of the new cultivar 'Madez' are most similar to the commercial cultivar, *Ilex* 'Mesid' (U.S. Plant Pat. No. 4,685). A comparison of 'Madez' with *Ilex* 'Mesid' is described in Chart 2.

CHART 2

| Characteristic | 'Madez' | 'Mesid' |
|---|---|---|
| Plant shape | Conical. | Globular. |
| General coloration of the juvenile foliage. | A combination of deep maroon and dark brown. | Burgundy. |

That which is claimed is:

1. A new and distinct variety of *Ilex* x *meserveae* plant named 'Madez', substantially as described and illustrated herein.

* * * * *